(12) United States Patent  
Liu et al.

(10) Patent No.: US 12,213,536 B2
(45) Date of Patent: Feb. 4, 2025

(54) ELECTRONIC CIGARETTE

(71) Applicant: CHINA TOBACCO HUNAN INDUSTRIAL CO., LTD., Hunan (CN)

(72) Inventors: Jianfu Liu, Hunan (CN); Kejun Zhong, Hunan (CN); Xiaoyi Guo, Hunan (CN); Wei Huang, Hunan (CN); Yuangang Dai, Hunan (CN); Xinqiang Yin, Hunan (CN); Jianhua Yi, Hunan (CN); Hong Yu, Hunan (CN); Yang Wang, Hunan (CN)

(73) Assignee: CHINA TOBACCO HUNAN INDUSTRIAL CO., LTD., Hunan (CN)

( * ) Notice: Subject to any disclaimer, the term of this patent is extended or adjusted under 35 U.S.C. 154(b) by 18 days.

(21) Appl. No.: 18/135,713

(22) Filed: Apr. 17, 2023

(65) Prior Publication Data

US 2023/0248057 A1    Aug. 10, 2023

Related U.S. Application Data

(62) Division of application No. 16/306,828, filed as application No. PCT/CN2016/110393 on Dec. 16, 2016, now Pat. No. 11,744,282.

(30) Foreign Application Priority Data

Jun. 27, 2016   (CN) .......................... 201620643868.8
Jun. 27, 2016   (CN) .......................... 201620644519.8

(51) Int. Cl.
*A24F 40/42*   (2020.01)
*A24F 7/00*    (2006.01)
(Continued)

(52) U.S. Cl.
CPC ................ *A24F 7/00* (2013.01); *A24F 40/05* (2020.01); *A24F 40/40* (2020.01); *A24F 40/42* (2020.01);
(Continued)

(58) Field of Classification Search
CPC ........... A24F 40/20; A24F 40/42; A24F 40/46
See application file for complete search history.

(56) References Cited

U.S. PATENT DOCUMENTS 7,832,410 B2   11/2010   Hon
8,915,254 B2   12/2014   Monsees et al.
(Continued)

FOREIGN PATENT DOCUMENTS

CN   201481582 U    5/2010
CN   202068931 U   12/2011
(Continued)

OTHER PUBLICATIONS

International Search Report issued in International Application No. PCT/CN2016/110393 dated Mar. 1, 2017, 6 pages.

*Primary Examiner* — Russell E Sparks
(74) *Attorney, Agent, or Firm* — MASCHOFF BRENNAN; Michael Mauriel

(57) ABSTRACT

An electronic cigarette, comprising a shell and a power supply installed in the shell, and the electronic cigarette further comprises a tobacco bin which is provided in the shell and communicates with the outside air, and a suction nozzle which communicates with the tobacco bin; and a piezoelectric ceramic piece which clings to the tobacco bin is provided in the shell, the piezoelectric ceramic piece is a bearing surface of the tobacco bin on which a tobacco material is loaded as well as a heating surface of the tobacco bin, and the piezoelectric ceramic piece is electrically connected with the power supply. The electronic cigarette has a
(Continued)

simple atomization mode and directly atomizes the tobacco material by means of the high frequency vibration and heat of the piezoelectric ceramic.

8 Claims, 10 Drawing Sheets

(51) Int. Cl.
*A24F 40/05* (2020.01)
*A24F 40/20* (2020.01)
*A24F 40/40* (2020.01)
*A24F 40/46* (2020.01)
*A61M 11/04* (2006.01)

(52) U.S. Cl.
CPC .............. *A24F 40/46* (2020.01); *A24F 40/20* (2020.01); *A61M 11/042* (2014.02)

(56) References Cited

U.S. PATENT DOCUMENTS

| | | | |
|---|---|---|---|
| 8,991,402 B2 | 3/2015 | Bowen et al. | |
| 9,254,002 B2 | 2/2016 | Chong et al. | |
| 9,675,107 B2 | 6/2017 | Levitz et al. | |
| 9,723,875 B2 | 8/2017 | Liu | |
| 10,179,215 B2 | 1/2019 | Raichman | |
| 10,492,527 B2 | 12/2019 | Liu et al. | |
| 10,531,687 B2 | 1/2020 | Liu et al. | |
| 10,874,144 B2 | 12/2020 | Powell | |
| 11,103,660 B2 | 8/2021 | Qiu | |
| 11,717,845 B2* | 8/2023 | Courbat .............. B05B 17/0684 239/4 |
| 11,744,282 B2 | 9/2023 | Liu et al. | |
| 2016/0338407 A1* | 11/2016 | Kerdemelidis ......... A24F 40/60 |
| 2017/0119059 A1 | 5/2017 | Zuber et al. | |
| 2018/0289908 A1 | 10/2018 | Marmur et al. | |

FOREIGN PATENT DOCUMENTS

| | | |
|---|---|---|
| CN | 203424304 U | 2/2014 |
| CN | 203633507 U | 6/2014 |
| CN | 204032356 U | 12/2014 |
| CN | 204317491 U | 5/2015 |
| CN | 204377936 U | 6/2015 |
| CN | 104983078 A | 10/2015 |
| CN | 105768238 A | 7/2016 |
| CN | 205757206 U | 12/2016 |
| CN | 205757207 A | 12/2016 |
| JP | 3141414 U | 5/2008 |
| WO | 2016/055653 A1 | 4/2016 |
| WO | 2018/041106 A1 | 3/2018 |

\* cited by examiner

ELECTRONIC CIGARETTE

CROSS REFERENCE TO RELATED APPLICATIONS

This application is a divisional of U.S. application Ser. No. 16/306,828 filed Dec. 3, 2018, which is a national phase application of international application number PCT/CN2016/110393 filed on Dec. 16, 2016, which claims priority to Chinese application number 201620643868.8 filed on Jun. 27, 2016 and Chinese application number 201620644519.8 filed on Jun. 27, 2016. The entire contents of these applications are hereby incorporated herein by reference.

TECHNICAL FIELD

The present invention belongs to an electronic cigarette, and is particularly suitable for solid tobacco materials.

BACKGROUND ART

The traditional electronic cigarette mainly uses electric heating wires, generally nickel-chromium alloy wires, iron-chromium-aluminum and other materials, and the electric heating wires will produce a lot of heat when being electrified to heat tobacco tar to realize atomization.

Traditional low-temperature cigarette also realize atomization by heating tobacco shreds or tobacco paste by electric heating material.

The electronic cigarette in the prior art has the following drawbacks in use:

1. When heating is carried out by using an electric heating material, the temperature is high and is generally higher than 200 degrees Celsius. At this time, if tobacco tar supply is insufficient, burnt taste or other peculiar smell is produced easily.

2. If the temperature is too high, hand scalding or mouth scalding and other problems are caused easily, and after the produced high-temperature smoke is inhaled, the oral cavity is injured. Moreover, the high temperature is liable to damage internal electronic components and battery, thereby affecting the service life of a smoking set.

3. The traditional electronic cigarette which heat tobacco tar using electric heating wires is also subjected to tobacco tar leakage risk.

CONTENTS OF INVENTION

In view of the above problems, the present invention aims at providing an electronic cigarette, which produces no burned taste or peculiar smell, avoids hand scalding or mouth scalding caused by overheating, and no tobacco tar leakage or backward tobacco tar suction occurs.

The technical solution adopted to solve the problems in the present invention is as follows; an electronic cigarette comprises a shell and a power supply installed in the shell, and the electronic cigarette further comprises a tobacco bin which is provided in the shell and communicates with the outside air, and a suction nozzle which communicates with the tobacco bin; and
a piezoelectric ceramic piece which clings to the tobacco bin is provided in the shell, the piezoelectric ceramic piece is a bearing surface of the tobacco bin on which a tobacco material is loaded as well as a heating surface of the tobacco bin, and the piezoelectric ceramic piece is electrically connected with the power supply.

In the above solution, the surface of the piezoelectric ceramic piece facing to the tobacco bin is an atomization surface, and the surface of the piezoelectric ceramic piece deviated from the tobacco bin is a conducting surface. Preferably, the tobacco material is tobacco paste, tobacco shreds or other solid materials. After the power supply is turned on, the tobacco material starts to be oscillated and heated under the action of the piezoelectric ceramic piece. The tobacco material is a solid below 60 degrees Celsius and is a solid-liquid mixture at 60-100 degrees Celsius, and the smoke starts to be volatilized when the temperature exceeds 120 degrees Celsius. The electronic cigarette atomizes the tobacco material by the high frequency vibration and heat produced by the piezoelectric ceramic piece under the action of a high frequency voltage. The airflow enters the tobacco bin and passes by the surface of the piezoelectric ceramic piece to take away the smoke from an air passage of the suction nozzle to be inhaled by the user.

In a specific solution, the piezoelectric ceramic piece is horizontally provided at the upper part of the shell, the tobacco bin is provided on the upper surface of the piezoelectric ceramic piece, the piezoelectric ceramic piece is used as the bottom of the tobacco bin, and the top of the tobacco bin is open.

In the above solution, the upper end of the tobacco bin is an open end, and the lower end of the tobacco bin is an ultrasonic atomization end. When the electronic cigarette is used, the tobacco material is placed in the tobacco bin and is in contact with the piezoelectric ceramic piece, and the user turns on the switch to make the piezoelectric ceramic piece to start working. After the tobacco material is used up, the tobacco material can be directly added. The electronic cigarette can be repeatedly used and is simple to operate, and the use cost is reduced.

Specifically, the shell comprises a top cover and a bottom cover detachably connected with the top cover;
a battery bin is provided in the bottom cover, a battery is provided in the battery bin, and a first elastic conducting piece which contacts the battery is provided at the top of the battery;
the piezoelectric ceramic piece is provided in the top cover, and a spring electrode which contacts the piezoelectric ceramic piece is provided on the bottom surface of the piezoelectric ceramic piece; and
in a non-working state, a gap is provided between the spring electrode and the first elastic conducting piece.

In the above solution, the upper surface of the piezoelectric ceramic piece is the atomization surface, and the lower surface of the piezoelectric ceramic piece is in contact with the spring electrode to serve as the conducting surface. In a working state, the first elastic conducting piece undergoes elastic deformation to be in contact with the spring electrode so as to connect the battery with the piezoelectric ceramic piece.

In order to conveniently replace the internal elements of the electronic cigarette, the top cover is detachably connected with the bottom cover through a connecting sleeve, the connecting sleeve is a cylindrical boss with a convex section, an electrode installing hole is provided in the top of the connecting sleeve, and the spring electrode is inserted in the electrode installing hole; and the connecting sleeve is in threaded connection with the top cover, and the connecting sleeve is in interference fit with the bottom cover.

Further, a piezoelectric ceramic piece fixing base made of silica gel is provided in the top cover. The material of the piezoelectric ceramic piece fixing base is required to be insulated and have certain elasticity so as to buffer the vibration of the piezoelectric ceramic piece in a working process.

A switch which controls the connection and disconnection of the piezoelectric ceramic piece and the power supply is provided at the bottom of the shell, and a second elastic conducting piece is provided between the switch and the power supply. As the switch is provided at the bottom of the smoking set, it is more convenient to use.

In a preferred solution, the suction nozzle is of hollow tubular structure, a through hole is provided in the side surface of the tobacco bin, and the suction nozzle is in fixed connection with the through hole in the side surface of the tobacco bin through a suction nozzle fixing sleeve.

In the above solution, the shell can be made into an oval shape so as to form a pipe-shaped electronic cigarette.

In another preferred solution, the suction nozzle is covered on the top of the tobacco bin and can be opened and closed.

Specifically, the shell comprises a top cover and a bottom cover detachably connected with the top cover, the top cover and the bottom cover are cylindrical, and an air inlet hole which communicates with the tobacco bin is provided in the side wall of the top cover:
the suction nozzle comprises a cylindrical base having a diameter being the same as that of the top cover and a columnar nozzle head located on the base;
both of the base and the nozzle head are of hollow structures, and the inner cavity of the nozzle head communicates with the inner cavity of the base; and
one side of the base is hinged with the top of the top cover, and the other side of the base is detachably connected with the top of the top cover.

In the above solution, the suction nozzle is opened and closed in a hinge manner, so it is convenient for the user to randomly rotate and invert the smoking set in use without worrying about that the tobacco material in the tobacco bin drops out from the smoking set.

Further, the diameter of the base is larger than the diameter of the nozzle head, a material blocking plug is fixed at the junction of the inner cavity of the base and the inner cavity of the nozzle head, the material blocking plug comprises a first cylindrical platform and a second cylindrical platform located on the first cylindrical platform and having a diameter smaller than that of the first cylindrical platform, at least one horizontal through hole is provided in the side wall of the first cylindrical platform, a vertical through hole is provided in the top of the second cylindrical platform, and the horizontal through hole communicates with the vertical through hole; and
the shoulder of the material blocking plug is clamped at the junction of the inner cavity of the base and the inner cavity of the nozzle head.

In the above solution, due to the application of the material blocking plug, the airflow enters the horizontal through hole along the edge of the inner wall of the tobacco bin, so that impurities of the tobacco material can be prevented from entering the oral cavity of the user together with the airflow to affect the user experience.

Further, a magnet is provided on the base, and the opening and closing of the suction nozzle can be realized by the attraction of the magnet to the top of the shell.

In another specific solution, the piezoelectric ceramic piece is vertically installed at the upper part of the shell, and the tobacco bin is provided on one side of the piezoelectric ceramic piece, and a tobacco bin cover capable of sealing the tobacco bin is provided at the tobacco bin, and an air inlet which communicates with the tobacco bin is provided in the tobacco bin cover.

Further, the shell comprises a body and a back cover detachably connected with the body; and
a battery and a control board electrically connected with the battery are provided in the shell, and the spring electrode is provided at the upper part of the control board:
and the piezoelectric ceramic piece is provided at the upper part of the body, and one side surface of the piezoelectric ceramic piece deviated from the tobacco bin is in contact with the spring electrode. Further, the piezoelectric ceramic piece fixing base is arranged at the upper part of the framework. The piezoelectric ceramic piece fixing base has a plurality of structures, as long as the piezoelectric ceramic piece can be fixed in principle. For example, a specific mode is as follows: the piezoelectric ceramic piece fixing base comprises an annular bracket which is in fixed connection with the body and a silica gel sleeve sheathed in the annular bracket, and a groove which fixes the piezoelectric ceramic piece is provided in the inner wall of the silica gel sleeve.

In order to conveniently wash the suction nozzle, the suction nozzle is detachably connected with the top of the body, and the connected joint between the suction nozzle and the top of the body is sealed by a sealing ring.

The tobacco bin cover can also be designed into a plurality of structures. In a preferred solution, the tobacco bin cover comprises an overturning cover hinged with the shell, and a first impaction device capable of pressing the tobacco material on the side surface of the piezoelectric ceramic piece is fixedly installed on the inner surface of the overturning cover.

An air inlet through hole is provided in the overturning cover, and the first impaction device is provided with an airflow passage which communicates the air inlet through hole with the tobacco bin.

In the above solution, the function of the first impaction device is to ensure more sufficient contact between the tobacco material and the piezoelectric ceramic piece. After the tobacco material is used up, the overturning cover can be overturned for direct addition of the tobacco material to the tobacco bin, and then the overturning cover can be closed for further use. The operation is simple, and the use cost is reduced.

The first impaction device is a telescopic spring box, which comprises an inner cover fixed to the inner surface of the overturning cover, a spring bracket which is in fixed connection with the inner cover, a first spring cover sheathed in the spring bracket and capable of moving horizontally, and a spring, wherein one end of the spring is connected with the inner cover, and the other end of the spring is connected with the first spring cover; and
the inner cover, the spring bracket and the first spring cover constitute a sealed hollow cavity structure so as to seal the spring in the hollow cavity; and a first air inlet pinhole is provided in a position corresponding to the air inlet through hole on the inner cover, and a first air outlet pinhole which communicates with the tobacco bin is provided in the first spring cover.

In another preferred design solution of the tobacco bin cover, the tobacco bin cover comprises a front cover which is in threaded connection with the shell, and a second impaction device capable of pressing the tobacco material on the side surface of the piezoelectric ceramic piece is in fixed connection with the inner side of the front cover;

a second air inlet pinhole is provided in the front cover, and the second impaction device is provided with an airflow passage which communicates the second air inlet pinhole with the tobacco bin; and after the front cover is screwed in the shell, the front cover is flush with the surface of the shell.

In the above solution, the tobacco bin cover is designed to be a screw type structure and is fixed and detached by screw engagement of threads. Moreover, after the front cover is screwed in the shell, the front cover is flush with the surface of the shell, therefore the appearance is smoother, and it is more convenient to carry.

The function of the second impaction device is to ensure more sufficient contact between the tobacco material and the piezoelectric ceramic piece.

The second impaction device comprises a hollow fixing ring sheathed on the inner side of the front cover, a second spring cover sheathed on the inner side of the fixing ring and capable of moving horizontally, and a spring, wherein one end of the spring is connected with the inner side of the front cover, and the other end of the spring is connected with the second spring cover; and the front cover, the fixing ring and the second spring cover constitute a sealed hollow cavity structure so as to seal the spring in the hollow cavity; and a second air outlet pinhole which communicates with the tobacco bin is provided in the second spring cover.

Further, the electronic cigarette further comprises solid tobacco material provided in the tobacco bin, and a cut groove is provided in the tobacco material. Due to the cut groove, when the tobacco material is atomized, the smoke can go out more smoothly.

The present invention has the following beneficial effects:

1. The atomization mode is simple, and the tobacco material is directly atomized by means of the high frequency vibration and heat of the piezoelectric ceramic piece.

2. The properties of the piezoelectric ceramic itself determine a relatively low atomization temperature of the smoking set, the atomization temperature does not exceed 200 degrees Celsius in general, and thus no burned taste or peculiar smell is produced, and the problem of hand scalding or mouth scalding caused by overheating of smoking set can be avoided.

3. The temperature of the produced smoke is not high, and thus the oral mucosa will not be injured.

4. The electronic cigarette is simple to use, the electronic cigarette can be used after the tobacco material is directly added to the piezoelectric ceramic piece, and after the tobacco material is used up, the tobacco material can be further directly added to the surface of the piezoelectric ceramic piece for further use.

5. As the atomized material is the solid tobacco paste, tobacco shreds or other tobacco materials, the problem of tobacco tar leakage or backward tobacco tar suction will not occur, and meanwhile no residues are attached to the piezoelectric ceramic piece due to carbonization.

6. The electronic cigarette has the advantages of being simple in structure, convenient to wash, clean and sanitary.

DESCRIPTION OF FIGURES

The present invention will be further illustrated below in combination with the drawings.

Reference signs: 1—shell, 2—first elastic conducting piece, 3—piezoelectric ceramic piece, 4—tobacco bin, 5—suction nozzle, 6—spring electrode, 7—connecting sleeve, 8—piezoelectric ceramic piece fixing base, 9—switch, 10—suction nozzle fixing sleeve. 11—top cover, 12—bottom cover, 13—battery, 14—air inlet hole, 15—second elastic conducting piece, 20—tobacco bin cover. 21—overturning cover, 22—air inlet through hole, 23—first impaction device, 24—first air inlet pinhole, 25—first air outlet pinhole, 26—front cover, 27—second impaction device, 28—second air inlet pinhole, 29—second air outlet pinhole, 51—base, 52—nozzle head, 53—material blocking plug, 54—magnet, 70—tobacco material, 71—electrode installing hole, 81—annular bracket, 82—silica gel sleeve, 100—sealing ring, 110—body, 120—back cover, 140—control board, 231—inner cover, 232—spring bracket, 233—first spring cover, 234—spring, 271—fixing ring, 272—second spring cover, 531—first cylindrical platform, 532—second cylindrical platform, 533—horizontal through hole, 531—vertical through hole, and 701—cut groove.

SPECIFIC MODE FOR CARRYING OUT THE INVENTION

Embodiment 1

Figure 1:
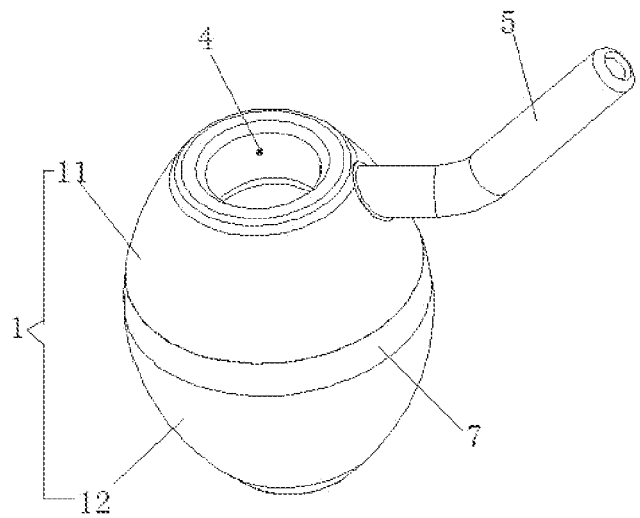
FIG. 1 is an appearance structure diagram of an electronic cigarette of an embodiment 1.
Figure 2:
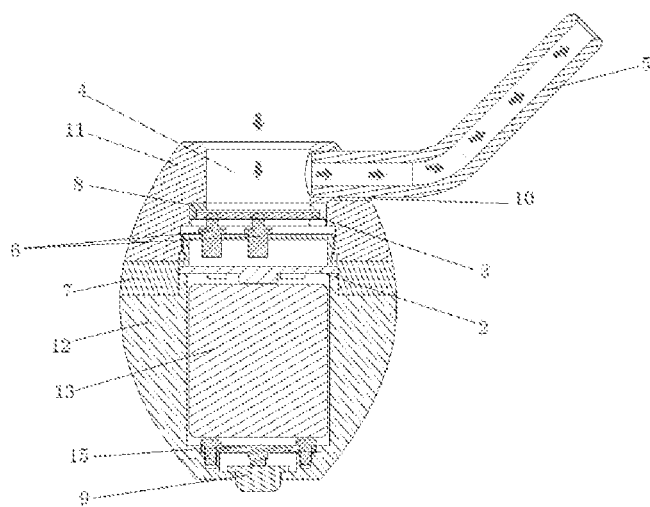
FIG. 2 is a section view of the embodiment 1.
Figure 3:
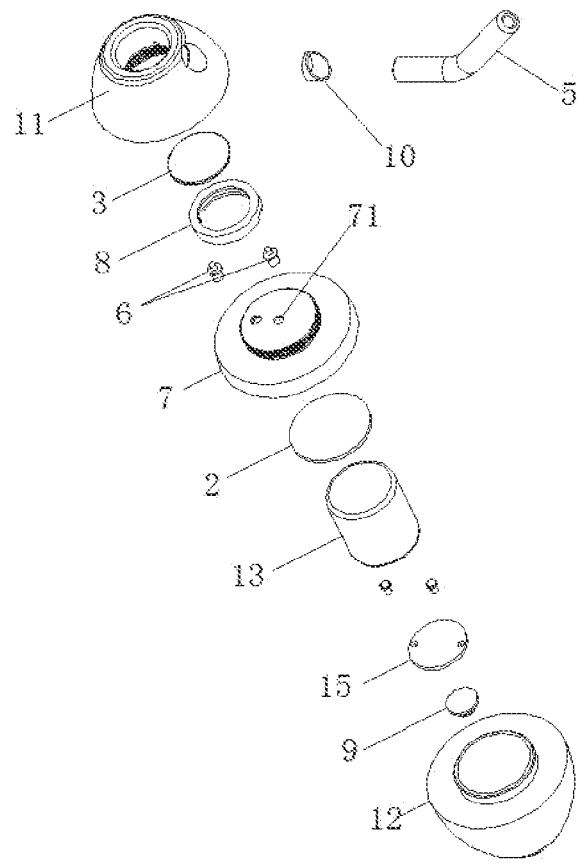
FIG. 3 is an explosive view of the embodiment 1.
Figure 4:
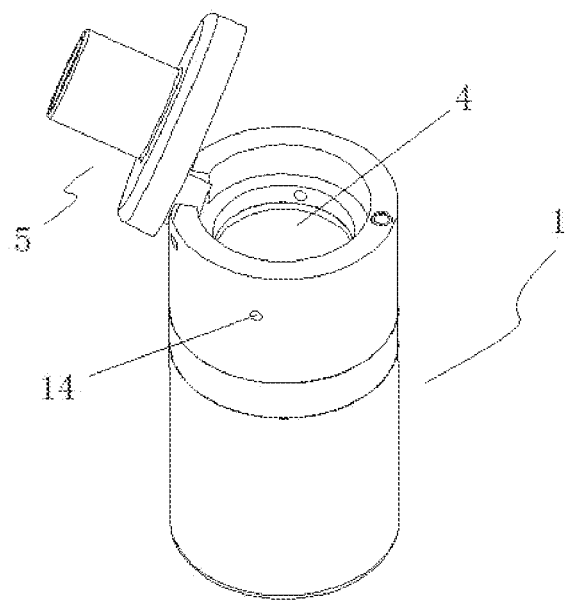
FIG. 4 is an appearance structure diagram of an electronic cigarette of an embodiment 2.
Figure 5:
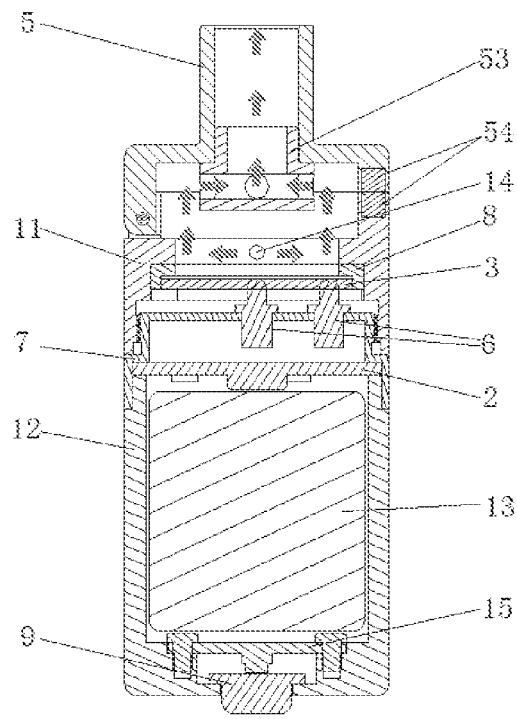
FIG. 5 is a section view of the embodiment 2.
Figure 6:
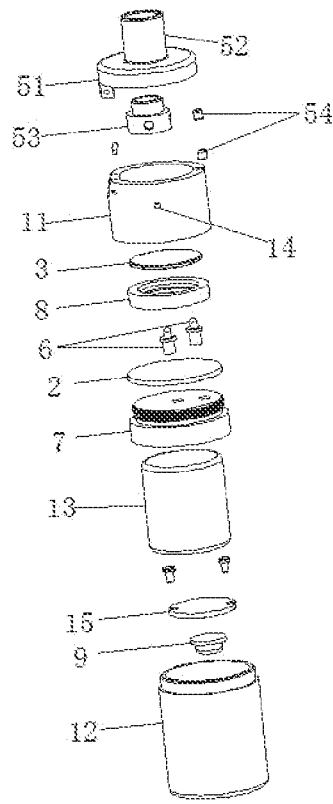
FIG. 6 is an explosive view of the embodiment 2.
Figure 7:
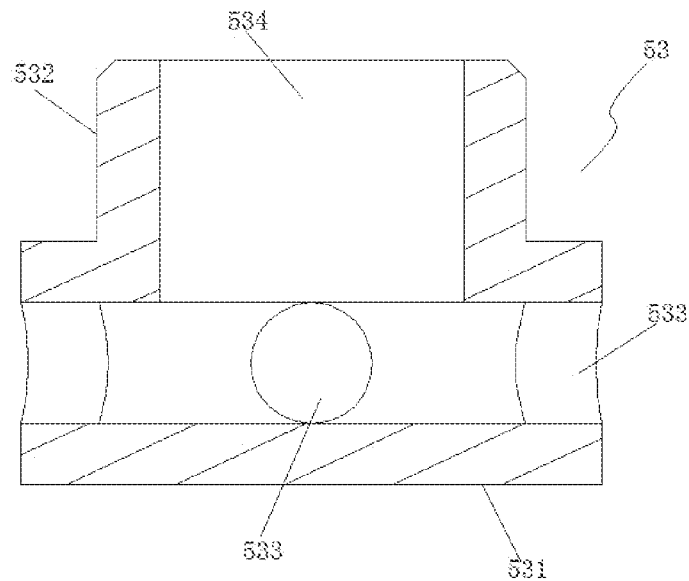
FIG. 7 is a structure diagram of a material blocking plug of the embodiment 2.
Figure 8:
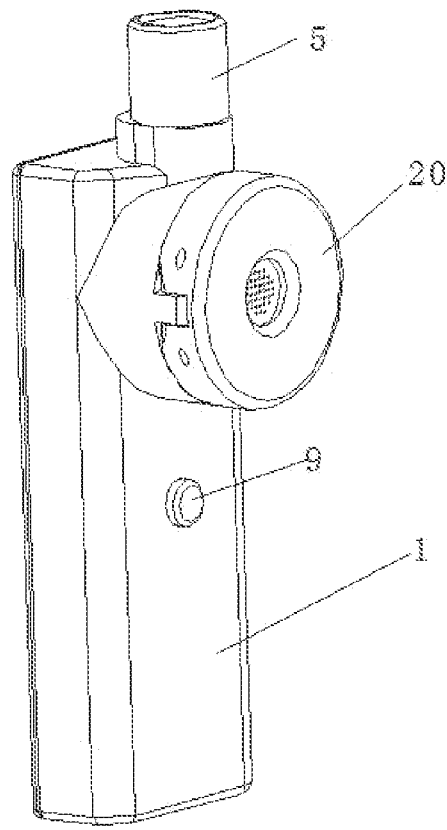
FIG. 8 is an appearance structure diagram of an electronic cigarette of an embodiment 3.
Figure 9:
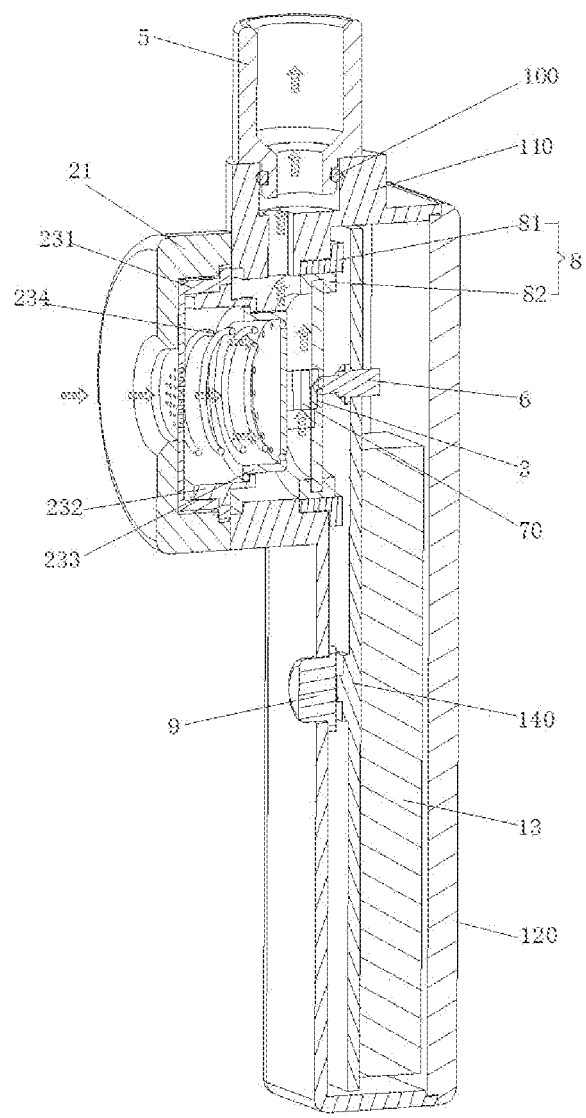
FIG. 9 is a section view of the embodiment 3.
Figure 10:
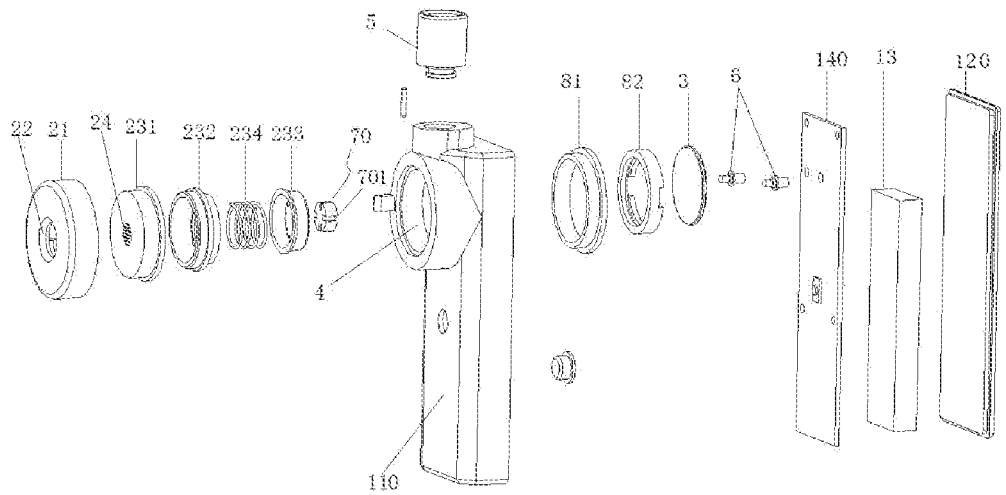
FIG. 10 is an explosive view of the embodiment 3.
Figure 11:
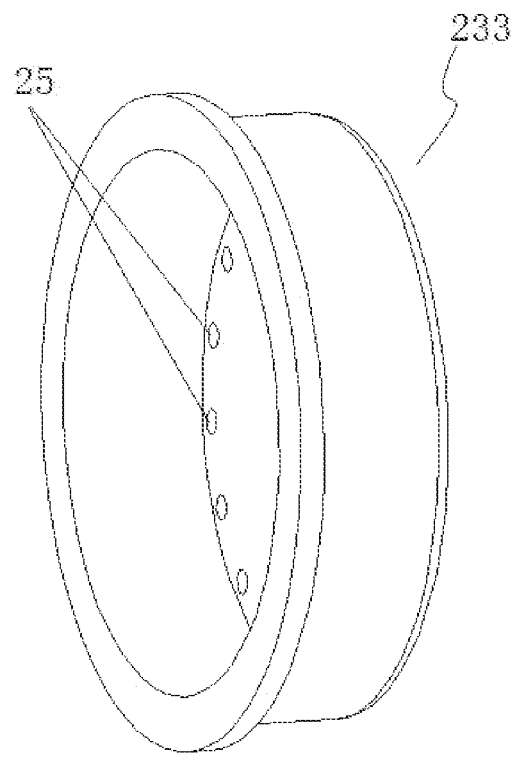
FIG. 11 is a structure diagram of a first spring cover.
Figure 12:
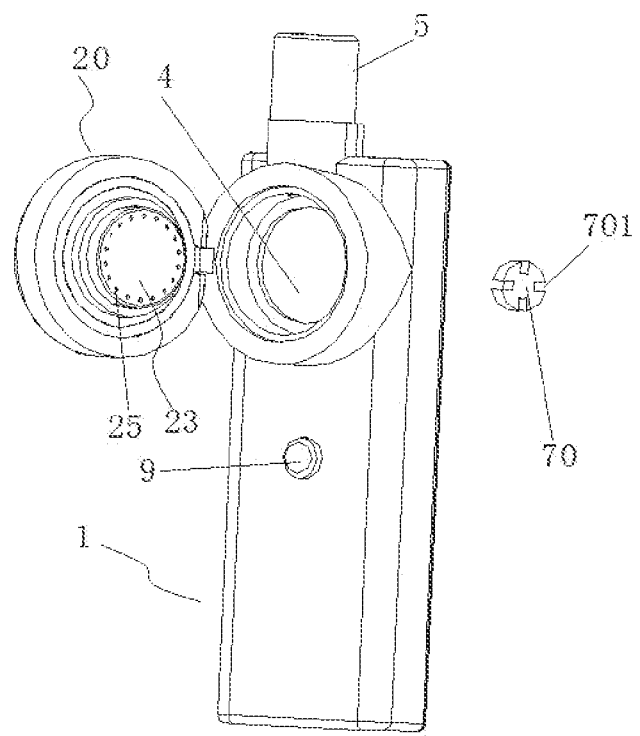
FIG. 12 is a state diagram after a tobacco bin cover is opened in the embodiment 3.
Figure 13:
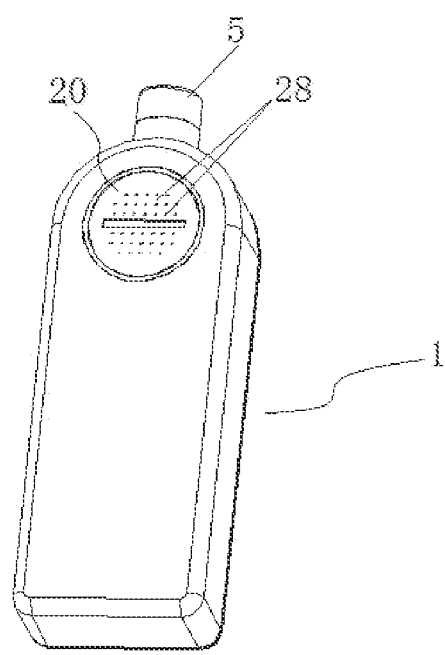
FIG. 13 is an appearance structure diagram of an electronic cigarette of an embodiment 4.
Figure 14:
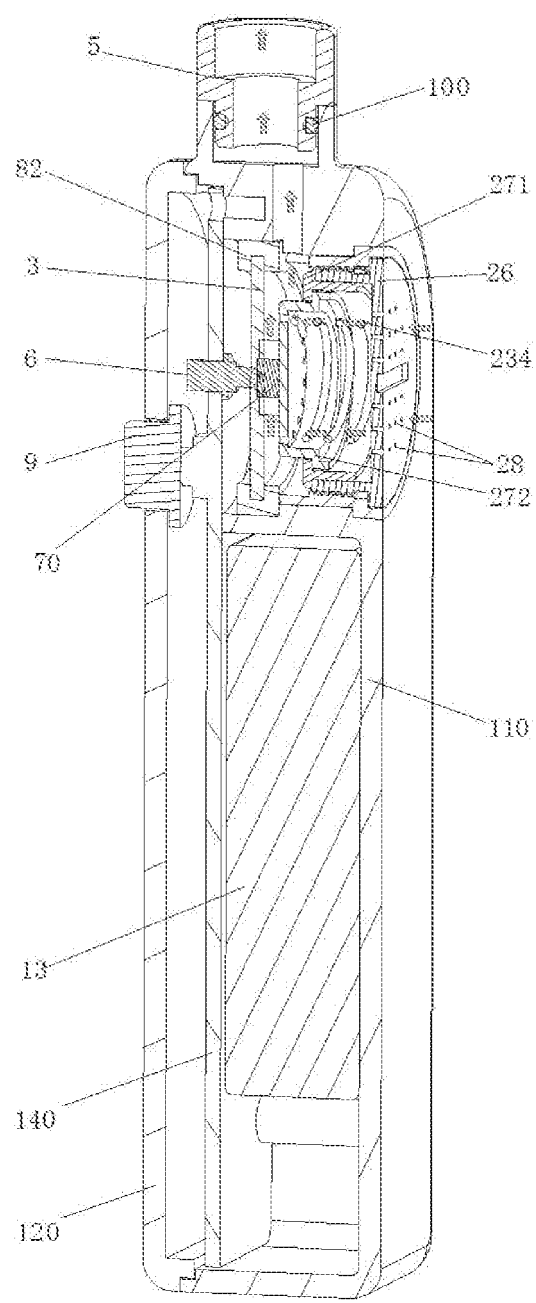
FIG. 14 is a section view of the embodiment 4.
Figure 15:
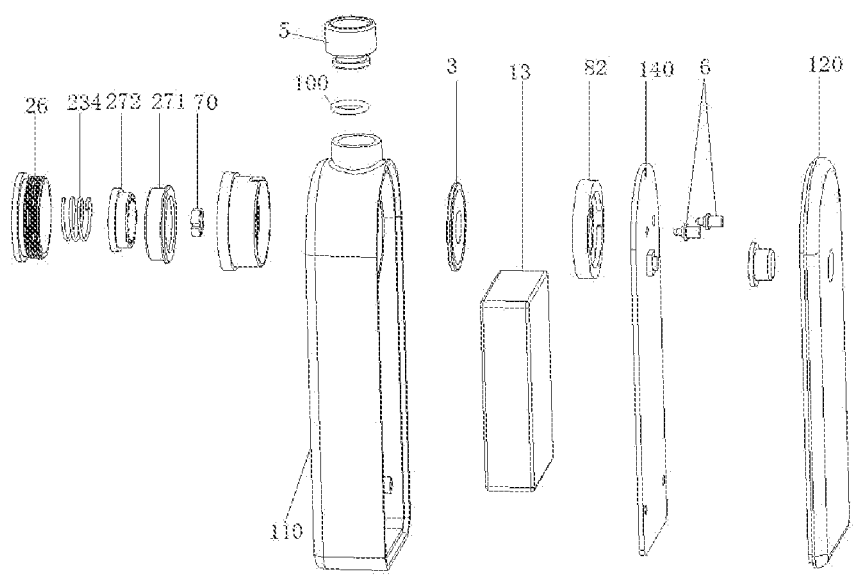
FIG. 15 is an explosive view of the embodiment 4.
Figure 16:
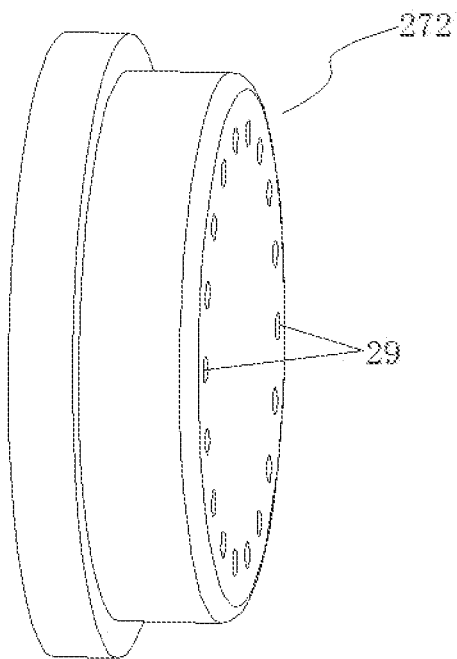
FIG. 16 is a structure diagram of a second spring cover.
Figure 17:
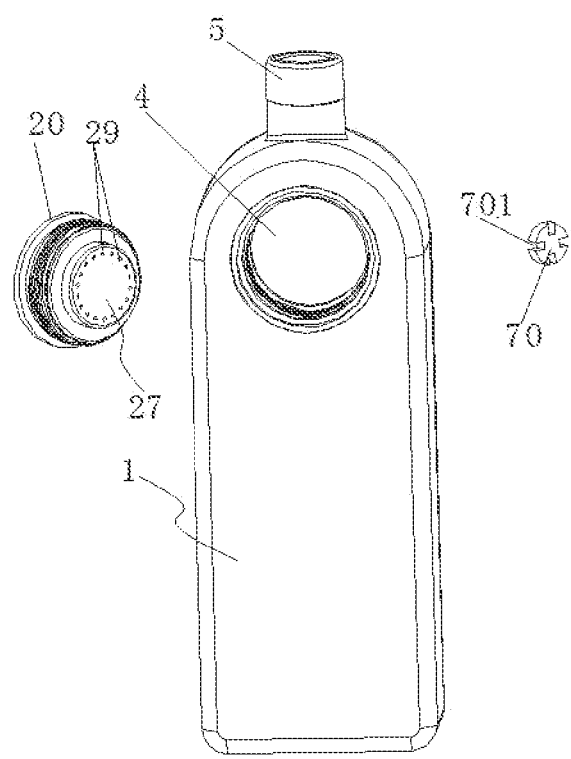
FIG. 17 is a state diagram after the tobacco bin cover is opened in the embodiment 4.

As shown in FIG. 1 to FIG. 3, an electronic cigarette comprises a shell 1, and the shell 1 comprises a top cover 11 and a bottom cover 12 detachably connected with the top cover 11. A battery bin is provided in the bottom cover 12, a battery 13 is provided in the battery bin, and a first elastic conducting piece 2 which contacts the battery 13 is provided at the top of the battery 13. The shell 1 can be made into an oval shape so as to form a pipe-shaped electronic cigarette.

The electronic cigarette further comprises a solid piezoelectric ceramic piece 3 (namely, when the electronic cigarette is vertically placed on a horizontal plane, the radial surface of the solid piezoelectric ceramic piece 3 is parallel to the horizontal plane) horizontally provided in the top cover 11, a tobacco bin 4 is provided on the upper surface of the piezoelectric ceramic piece 3, the piezoelectric ceramic piece 3 is used as the bottom of the tobacco bin, and the top of the tobacco bin 4 is open. A piezoelectric ceramic piece fixing base 8 made of silica gel is provided in the top cover 11.

The top cover 11 is detachably connected with the bottom cover 12 through a connecting sleeve 7. The connecting sleeve 7 is in threaded connection with the top cover 11, and the connecting sleeve 7 is in interference fit with the bottom cover 12.

The connecting sleeve 7 is a cylindrical boss with a convex section, an electrode installing hole 71 is provided in the top of the connecting sleeve 7, and the spring electrode 6 is inserted in the electrode installing hole 71. The bottom surface of the piezoelectric ceramic piece 3 is in contact with the spring electrode 6. A gap is provided between the bottom surface of the piezoelectric ceramic piece 3 and the top of the connecting sleeve 7 for heat dissipation. The piezoelectric ceramic piece 3 is electrically connected with the first elastic conducting piece 2 through the spring electrode 6. In a non-working state, a gap is provided between the spring electrode 6 and the first elastic conducting piece 2. The upper surface of the piezoelectric ceramic piece 3 is an atomization surface, and the lower surface of the piezoelectric ceramic piece 3 is in contact with the spring electrode 6 to serve as a conducting surface. In a working state, the first elastic conducting piece 2 undergoes elastic deformation to be in contact with the spring electrode 6 so as to connect the battery 13 with the piezoelectric ceramic piece 3.

A switch 9 which controls the connection and disconnection of the piezoelectric ceramic piece 3 and the battery 13 is provided at the bottom of the shell 1, and a second elastic conducting piece 15 is provided between the switch 9 and the battery 13.

The electronic cigarette further comprises a suction nozzle 5 which communicates with the tobacco bin 4. The suction nozzle 5 is of hollow tubular structure. A through hole is provided in the side surface of the tobacco bin 4, and the suction nozzle 5 is in fixed connection with the through hole in the side surface of the tobacco bin 4 through a suction nozzle fixing sleeve 10.

The upper end of the tobacco bin 4 is an open end, and the lower end of the tobacco bin is an ultrasonic atomization end. When the electronic cigarette is used, the tobacco material is placed in the tobacco bin 4 and is in contact with the piezoelectric ceramic piece 3, and the user turns on the switch 9 to make the piezoelectric ceramic piece 3 to start working. After the piezoelectric ceramic piece 3 is started to work, the piezoelectric ceramic piece 3 will produce certain heat by itself, produce high frequency oscillation and transfers the heat to the tobacco material so as to produce smoke by the tobacco material under the oscillation of the piezoelectric ceramic piece 3 and the heating of the heat. The airflow passes by the surface of the piezoelectric ceramic piece 3 to take away the smoke from an air passage of the suction nozzle to be inhaled by the user. After the tobacco material is used up, the tobacco material can be directly added. The tobacco material comprises tobacco paste or tobacco shreds.

Embodiment 2

As shown in FIG. 4 to FIG. 7, the embodiment 1 is repeated, the difference lies in that, the suction nozzle 5 is covered on the top of the tobacco bin 4 and can be opened and closed.

The top cover 11 and the bottom cover 12 are cylindrical, and an air inlet hole 14 which communicates with the tobacco bin 4 is provided in the side wall of the top cover 11.

The suction nozzle 5 comprises a cylindrical base 51 having a diameter being the same as that of the top cover 11 and a columnar nozzle head 52 located on the base 51.

Both of the base 51 and the nozzle head 52 are of hollow structures, and the inner cavity of the nozzle head 52 communicates with the inner cavity of the base 51.

One side of the base 51 is hinged with the top of the top cover 11, and the other side of the base 51 is detachably connected with the top of the top cover 11. The preferred detachable connection manner is that, a magnet 54 is provided on the base 51, and the opening and closing of the suction nozzle 5 can be realized by the attraction of the magnet 54 to the top of the shell 1.

The diameter of the base 51 is larger than the diameter of the nozzle head 52. A material blocking plug 53 is fixed at the junction of the inner cavity of the base 51 and the inner cavity of the nozzle head 52. The material blocking plug 53 comprises a first cylindrical platform 531 and a second cylindrical platform 532 located on the first cylindrical platform 531 and having a diameter smaller than that of the first cylindrical platform 531. At least one horizontal through hole 533 is provided in the side wall of the first cylindrical platform 531, a vertical through hole 534 is provided in the top of the second cylindrical platform 532, and the horizontal through hole 533 communicates with the vertical through hole 534.

The shoulder of the material blocking plug 53 is clamped at the junction of the inner cavity of the base 51 and the inner cavity of the nozzle head 52.

Embodiment 3

As shown in FIG. 8 to FIG. 12, an electronic cigarette comprises a shell 1, and the shell 1 comprises a body 110 and a back cover 120 detachably connected with the body 110. A battery 13 and a control board 140 electrically connected with the battery 13 are provided in the shell 1. A spring electrode 6 is provided at the upper part of the control board 140.

The electronic cigarette further comprises a piezoelectric ceramic piece 3 (namely, when the electronic cigarette is vertically placed on a horizontal plane, the radial surface of the solid piezoelectric ceramic piece 3 is vertical to the horizontal plane) vertically installed at the upper part of the body 110, and a tobacco bin 4 is provided on one side of the piezoelectric ceramic piece 3. The piezoelectric ceramic piece 3 is used as the heating surface of the tobacco bin 4. One side surface of the piezoelectric ceramic piece 3 deviated from the tobacco bin 4 is in contact with the spring electrode 6. A gap is provided between the piezoelectric ceramic piece 3 and the control board 140 for heat dissipation.

A switch 9 which controls the connection and disconnection of the piezoelectric ceramic piece 3 and a power supply is provided at the middle of the shell 1.

The electronic cigarette further comprises a suction nozzle 5 which communicates with the tobacco bin 4. The suction nozzle 5 is detachably connected with the top of the body 110, and the connecting joint between the suction nozzle 5 and the top of the body 110 is sealed by a sealing ring 10.

The electronic cigarette further comprises a solid tobacco material 70 provided in the tobacco bin 4, and a cut groove 701 is provided in the tobacco material 70.

In a preferred solution, a piezoelectric ceramic piece fixing base 8 is provided at the upper part of the body 110. The piezoelectric ceramic piece fixing base 8 has a plurality of structures, as long as the piezoelectric ceramic piece 3 can be fixed in principle. A specific mode is as follows: the piezoelectric ceramic piece fixing base comprises an annular bracket 81 which is in fixed connection with the body 110 and a silica gel sleeve 82 sheathed in the annular bracket 81, and a groove which fixes the piezoelectric ceramic piece 3 is provided in the inner wall of the silica gel sleeve 82.

A tobacco bin cover 20 capable of sealing the tobacco bin 4 is provided at the tobacco bin 4. The tobacco bin cover 20 comprises an overturning cover 21 hinged with the shell 1. A first impaction device 23 capable of pressing the tobacco material 70 on the side surface of the piezoelectric ceramic piece 3 is fixedly installed on the inner surface of the overturning cover 21. The first impaction device 23 is a telescopic spring box, which comprises an inner cover 231 fixed to the inner surface of the overturning cover 21, a spring bracket 232 which is in fixed connection with the inner cover 231, a first spring cover 233 sheathed in the spring bracket 232 and capable of moving horizontally, and a spring 234, wherein one end of the spring 234 is connected with the inner cover 231, and the other end of the spring 234 is connected with the first spring cover 233.

The inner cover 231, the spring bracket 232 and the first spring cover 233 constitute a sealed hollow cavity structure so as to seal the spring 234 in the hollow cavity.

An air inlet through hole 22 is provided in the overturning cover 21, a first air inlet pinhole 24 is provided, in a position corresponding to the air inlet through hole 22, in the inner cover 231, and a first air outlet pinhole 25 which communicates with the tobacco bin 4 is provided in the first spring cover 233.

The surface of the piezoelectric ceramic piece 3 facing to the tobacco bin 4 is an atomization surface, and the surface of the piezoelectric ceramic piece deviated from the tobacco bin 4 is a conducting surface. The tobacco material 70 is sealed in the tobacco bin 4 by the tobacco bin cover 20, and after the power supply is turned on, the tobacco material 70 starts to be oscillated and heated under the action of the piezoelectric ceramic piece 3. The tobacco material 70 is a solid material in general, the tobacco material 70 is a solid below 60 degrees Celsius and is a solid-liquid mixture at 60-100 degrees Celsius, and the smoke starts to be volatilized when the temperature exceeds 120 degrees Celsius. The electronic cigarette atomizes the tobacco material 70 by the high frequency vibration and heat produced by the piezoelectric ceramic piece 3 under the action of a high frequency voltage. The airflow enters from the air inlet in the tobacco bin cover 20 and passes by the surface of the piezoelectric ceramic piece 3 to take away the smoke from an air passage of the suction nozzle to be inhaled by the user.

Embodiment 4

As shown in FIG. 13 to FIG. 17, the embodiment 1 is repeated, the difference lies in that, the tobacco bin cover 20 comprises a front cover 26 which is in threaded connection with the shell. A second impaction device 27 capable of pressing the tobacco material 70 on the side surface of the piezoelectric ceramic piece 3 in fixed connection with the inner side of the front cover 26.

The second impaction device 27 comprises a hollow fixing ring 271 sheathed on the inner side of the front cover 26, a second spring cover 272 sheathed on the inner side of the fixing ring 271 and capable of moving horizontally, and a spring 234, wherein one end of the spring 234 is connected with the inner side of the front cover 26, and the other end of the spring is connected with the second spring cover 272.

The front cover 26, the fixing ring 271 and the second spring cover 272 constitute a sealed hollow cavity structure so as to seal the spring 234 in the hollow cavity. A second air inlet pinhole 28 is provided in the front cover 26, and a second air outlet pinhole 29 which communicates with the tobacco bin 4 is provided in the second spring cover 272.

The tobacco bin cover 20 is designed to be of screw type and is fixed and detached by spiral occlusion of threads. After the front cover 26 is screwed in the shell, the front cover is flush with the surface of the shell 1, therefore the appearance is smoother, and it is more convenient to carry.

The invention claimed is:

1. An electronic cigarette, comprising a shell and a power supply installed in the shell, wherein:
    the electronic cigarette further comprises a tobacco bin which is provided in the shell and communicates with an outside air, and a suction nozzle which communicates with the tobacco bin; and
    a piezoelectric ceramic piece which clings to the tobacco bin is provided in the shell,
    the piezoelectric ceramic piece is a bearing surface of the tobacco bin on which a tobacco material is loaded as well as a heating surface of the tobacco bin, wherein the piezoelectric ceramic piece is vertically installed at an upper part of the shell, and the tobacco bin is provided on one side of the piezoelectric ceramic piece;
    a tobacco bin cover capable of sealing the tobacco bin is provided at the tobacco bin, and an air inlet which communicates with the tobacco bin is provided in the tobacco bin cover;
    and the piezoelectric ceramic piece is electrically connected with the power supply.

2. The electronic cigarette of claim 1, wherein the shell comprises a body and a back cover detachably connected with the body; and
    a battery and a control board electrically connected with the battery are provided in the shell, and a spring electrode is provided at an upper part of the control board; and
    the piezoelectric ceramic piece is provided at an upper part of the body, and one side surface of the piezoelectric ceramic piece deviated from the tobacco bin is in contact with the spring electrode.

3. The electronic cigarette of claim 2, wherein a piezoelectric ceramic piece fixing base is provided at the upper part of the body.

4. The electronic cigarette of claim 2, wherein the suction nozzle is detachably connected with a top of the body, and a connected joint between the suction nozzle and the top of the body is sealed by a sealing ring.

5. The electronic cigarette of claim 1, wherein the tobacco bin cover comprises an overturning cover hinged with the shell and an impaction device capable of pressing the tobacco material on the side surface of the piezoelectric ceramic piece is fixedly installed on an inner surface of the overturning cover;
    an air inlet through hole is provided in the overturning cover, and the impaction device is provided with an airflow passage which communicates the air inlet through hole with the tobacco bin.

6. The electronic cigarette of claim 5, wherein the impaction device is a telescopic spring box, which comprises an inner cover fixed to the inner surface of the overturning cover, a spring bracket which is in fixed connection with the inner cover, a first spring cover sheathed in the spring bracket and capable of moving horizontally, and a spring, wherein one end of the spring is connected with the inner cover, and another end of the spring is connected with the first spring cover; and the inner cover, the spring bracket and the first spring cover constitute a sealed hollow cavity structure so as to seal the spring in a hollow cavity; and a first air inlet pinhole is provided, in a position corresponding to the air inlet through hole, in the inner cover, and a first air outlet pinhole which communicates with the tobacco bin is provided in the first spring cover.

7. The electronic cigarette of claim 1, wherein the tobacco bin cover comprises a front cover which is in threaded connection with the shell, and an impaction device capable of pressing the tobacco material on the side surface of the piezoelectric ceramic piece is in fixed connection with an inner side of the front cover;

a second air inlet pinhole is provided in the front cover, and the impaction device is provided with an airflow passage which communicates the second air inlet pinhole with the tobacco bin; and after the front cover is screwed in the shell, the front cover is flush with a surface of the shell.

8. The electronic cigarette of claim 7, wherein the impaction device comprises a hollow fixing ring sheathed on the inner side of the front cover, a second spring cover sheathed on an inner side of the fixing ring and capable of moving horizontally, and a spring, wherein one end of the spring is connected with the inner side of the front cover, and another end of the spring is connected with the second spring cover; and the front cover, the fixing ring and the second spring cover constitute a sealed hollow cavity structure so as to seal the spring in the hollow cavity; and a second air outlet pinhole which communicates with the tobacco bin is provided in the second spring cover.

\* \* \* \* \*